(12) United States Patent
Bachmann et al.

(10) Patent No.: US 10,874,504 B2
(45) Date of Patent: Dec. 29, 2020

(54) DEVICE FOR THE TRANSPLANTATION OF A DESCEMET'S MEMBRANE

(71) Applicant: Universitaet Zu Koeln, Cologne (DE)

(72) Inventors: Bjoern Bachmann, Cologne (DE); Sebastian Siebelmann, Solingen (DE); Claus Cursiefen, Cologne (DE)

(73) Assignee: UNIVERSITAET ZU KOELN, Cologne (DE)

( * ) Notice: Subject to any disclaimer, the term of this patent is extended or adjusted under 35 U.S.C. 154(b) by 109 days.

(21) Appl. No.: 16/312,473

(22) PCT Filed: Jun. 27, 2017

(86) PCT No.: PCT/EP2017/000748
§ 371 (c)(1),
(2) Date: Dec. 21, 2018

(87) PCT Pub. No.: WO2018/001558
PCT Pub. Date: Jan. 4, 2018

(65) Prior Publication Data
US 2019/0125520 A1    May 2, 2019

(30) Foreign Application Priority Data
Jun. 27, 2016 (DE) .................. 10 2016 007 738

(51) Int. Cl.
*A61F 2/14* (2006.01)
*A61F 9/007* (2006.01)

(52) U.S. Cl.
CPC .............. *A61F 2/148* (2013.01); *A61F 9/007* (2013.01); *A61F 2/147* (2013.01)

(58) Field of Classification Search
CPC ................... A61F 2/148; A61F 9/007
See application file for complete search history.

(56) References Cited

U.S. PATENT DOCUMENTS

2008/0281341 A1  11/2008  Miller et al.
2012/0226286 A1  9/2012  Weston et al.

FOREIGN PATENT DOCUMENTS

| DE | 102010051458 A1 | 5/2012 |
| EP | 2491890 A1 | 8/2012 |
| WO | 2007/132332 A2 | 11/2007 |

*Primary Examiner* — Melanie R Tyson
(74) *Attorney, Agent, or Firm* — Norris McLaughlin, P.A.

(57) ABSTRACT

A device for the transplantation of a Descemet's membrane includes a longitudinal tube having an inner cavity, an inlet opening through which it is possible to introduce the Descemet's membrane into the device, and an outlet opening through which it is possible to eject the Descemet's membrane from the device, especially into the anterior eye chamber of a patient, wherein the device also includes, at least in the region of the outlet opening, a separation element which protrudes from the inner wall region of the tube into the cavity, especially a first separation element, the separation element dividing the cavity at least regionally, in particular dividing it in a region close to the separation element.

15 Claims, 4 Drawing Sheets

DEVICE FOR THE TRANSPLANTATION OF A DESCEMET'S MEMBRANE

BACKGROUND OF THE INVENTION

The invention relates to a device for the transplantation of a Descemet's membrane, comprising a longitudinal tube having an inner cavity, an inlet opening through which it is possible to introduce the Descemet's membrane into the device, and an outlet opening through which it is possible to eject the Descemet's membrane from the device, especially into the anterior eye chamber of a patient.

Devices of this type are known in the prior art, for example from DE 10 2010 051 458 B4, and are used as part of an operation referred to as DMEK (Descemet's membrane endothelial keratoplasty) order to insert the Descemet's membrane with endothelium originating from a donor eye into a recipient eye, after its affected Descemet's membrane has been removed. The device known here has a circular inner and outer cross section and has merely a cross-sectional tapering along the longitudinal direction of extension in order to facilitate the introduction of the membrane at the inlet opening having the larger cross section and to assist the introduction of the device into the anterior chamber at the outlet opening which is smaller in cross section.

In said operation, the anterior chamber of the eye is opened with a short incision, the affected Descemet's membrane is scraped out and removed, and the donor Descemet's membrane is inserted into the anterior chamber using the device. As a rule in operations up to now, this is done with the membrane being in a state in which it is wound up to form a single-axis winding. Such a single-axis winding is introduced into the device, for example by insertion or inward suction, and also introduced as winding into the anterior chamber through the outlet opening of the device. The single-axis winding lying in the anterior chamber must then be unrolled in order to obtain the planar membrane and, after this, said membrane is pressed against the cornea by means of an air bubble in order to adhere there.

A single-axis winding is understood here to mean that the membrane surface is wound up around a single axis and, in this case, the end of the membrane that is lying in the winding direction thus lies over the other end or the membrane surface.

SUMMARY OF THE INVENTION

In said operation, a problem is that the Descemet's membrane has the tendency to automatically wind itself up to form a single-axis winding. After its preparation for transplantation preparation, the membrane is therefore generally present as such a winding and must be manually unwound by the surgeon after introduction into the anterior chamber of the eye, this being achieved in part using instruments introduced into the anterior chamber and/or with the aid of an air bubble and/or external pressure on the cornea. This procedure is time-consuming, can damage the transplant, and is stressful for the eye (increased risk of complications). Moreover, there is the risk that the front side/reverse side orientation is lost, resulting in lack of functionality of the transplantation.

It is therefore an object of the present invention to provide a device which facilitates the introduction of a Descemet's membrane into the anterior chamber of the eye in a DMEK operation and which in particular inherently makes the unrolling of the membrane in the eye more rapid, more safe, more standardized and also more simple.

According to the invention, this object is achieved using a generic device in which the tube has, at least in the region of the outlet opening, a separation element which protrudes from the inner wall region of the tube into the cavity, especially a first separation element, said separation element dividing the cavity at least regionally, in particular dividing it in a region close to the separation element.

The thinking underlying this achievement is that the tendency of the membrane to automatically wind itself up can also be utilized to wind up the Descemet's membrane to form a double-axis winding in which there thus arises a first subwinding around a first axis and a second subwinding around a second axis parallel thereto and both windings are connected to one another by a membrane surface portion. As a result, the overlap in the subwindings is lower than in the case of a single-axis winding, and so such a double-axis winding is not as stable in the long term as a single-axis winding and can also be reorganized to form the single-axis winding during a manipulation on the winding during the transplantation.

It has become apparent that a double-axis winding, if introduced successfully into the eye, can be unrolled more easily, and thus spread out to form the planar membrane, than is the case with a single-axis winding.

The invention achieves at least the maintenance of a double-axially arranged winding, and in a preferred embodiment also the formation of such a winding from an originally single-axis winding.

The stated separation element, which is situated at least in the region of the outlet opening, causes here a double-axis winding, which is present in said region and which was either inserted in this way into the device or is preferably even formed therein from a single-axis winding according to an embodiment discussed later, to stabilize and to not automatically reorganize even during introduction into the anterior chamber.

This is because, owing to its arrangement projecting from the inner wall, the separation element fits, in the case of the double-axis winding arranged there, between the two windings and thus prevents a membrane surface portion of one of the windings from being able to slide over the other winding.

The separation element thus separates both the cavity of the tube in the region of the outlet opening and, as a result, the two windings.

Here, it can be envisaged in the invention that the cavity is, in an environment around the outlet region that extends axially in the longitudinal direction of the tube, divided in an upper region into two laterally adjacent subcavities which are separated by the in particular first separation element and which are connected to one another in an underlying region. Thus, the effect of this arrangement is that each of the two subwindings lies in one of the two subcavities formed and the membrane surface region connecting the windings can extend in the stated underlying region between the windings.

With respect to the directions specified as part of this description, it must be stated that these refer to an orientation of the device, in which it is used as intended in an operation. In such a DMEK operation, the patient generally lies on his/her back and looks upward; the optical axis of the eye is thus oriented at least substantially vertically based on the Earth reference frame, which also forms the reference frame for the subsequent specified directions for the device.

The stated lateral arrangement of the subcavities thus means that they lie next to one another in a horizontal direction. In this connection, the separation element mentioned at the start is preferably arranged such that it extends into the cavity in a vertical direction from top to bottom proceeding from the upper inner wall of the tube. Said separation element can be a first separation element of the device, since a second one can also be envisaged in an embodiment described later. However, said separation element can also be the sole one. The optional second separation element lies at the bottom in the tube and extends in an upward direction from the inner wall of the tube. The details given (top/bottom/lateral) refer to a viewing of the cross section perpendicular to the longitudinal direction of extension of the tube, unless expressly described otherwise.

It can be envisaged in the invention that the connection of the subcavities is arranged below the separation element, in particular below the horizontal central plane of the outlet opening, especially when no second separation element is envisaged.

Preferably, the device is designed such that the tube has at least in the region of the outlet opening, possibly across its entire extent, a flattened outer cross section (viewed perpendicularly to the direction of extension). The nature of the flattening is preferably such that the tube has a smaller cross-sectional extent in the vertical direction (height) than in the horizontal direction (width), and is preferably oval or elliptic. Preferably, the ratio of vertical extent to horizontal extent, or of height to width, can be in the range of values from 0.5 to 0.8. This is advantageous because the incision in the eye to open the anterior chamber is made horizontally and is thus, owing to the smaller height of the tube in comparison with the width, only spread in the height direction to the absolutely necessary extent. This is already an advantage over circular cross sections of prior-art devices.

However, this is associated with a reduction in the inner circumference of the tube, and this can restrict the uptake of the double-axis winding, depending on the membrane diameter. Therefore, in a preferred further development, it can be envisaged in the invention that the inner cross section of the tube, at least in the region of the outlet opening, deviates in its shape congruence (with the exception of size scaling) from the outer cross section not only by the connection of the separation element, but also in other regions. This can be achieved when the inner wall does not always follow the outer wall equidistantly, but has in regions beyond the connection of the separation element an at least single-peak waviness in the circumferential direction. Such a waviness enlarges the circumferential length of the inner wall, and, as a result, the membrane surface can lie better along it, in particular overlaps in the two subwindings can thus be better avoided, further facilitating the subsequent unwinding in the anterior chamber.

Preferably, it is envisaged in the invention that the tube, at least in the region of the outlet opening, has a second separation element which protrudes into the cavity from the inner wall region of the tube and which divides the cavity at least regionally, in particular divides it in a region close to the second separation element, with the second separation element being opposite the first separation element, in particular both separation elements being around the vertical central plane of the tube, preferably in a symmetrical manner. Said second separation element can form a wave crest in the context of the aforementioned embodiment and preferably have a steadily guided surface.

Owing to said second separation element, the surface region of the membrane in the device that connects the subwindings is pushed in an upward direction to the first separation element, resulting in the respective subwindings being further unwound, since membrane surfaces are pulled off from these as a result of this shift. This further unwinding of the membrane already taking place in the device close to the outlet opening promotes the later further unwinding in the anterior chamber. It can be envisaged that the second separation element has a coating or surface quality (smoothness) which protects the endothelial layer of the Descemet's membrane. The tube or device can also, for example, be composed of PTFE (polytetrafluoroethylene) in whole or in subregions.

It can also be envisaged in the invention that, at least in the region of the outlet opening, the in particular first separation element has on its bottom region or end a recess which points upward (becomes upwardly deeper). Such a recess can also be formed in conjunction with the branching embodiment below, but can also be formed independently thereof. For example, the recess can also be formed in a cross-sectional thickening of the first separation element, especially a bottom cross-sectional thickening. This embodiment can also be envisaged without a second separation element in order to provide space for a membrane surface region between the subwindings that automatically arches upward.

In a further development, it can be envisaged in the invention that, at least in the region of the outlet opening, the in particular first separation element is branched on its bottom end and forms two arms on both sides of the vertical central plane. This configuration of the arms further promotes the stabilization of the double-axis winding, in particular the lower surfaces of the arms bring about a guidance of the membrane surface.

Preferably, at least in the region of the outlet opening, each of the arms can form a curve which points upward. Such a curve can cause each of the two subwindings of a double-axis winding to lie around an arm end, thereby preventing membrane surface regions from overlapping and from lying on top of one another. Preferably, the arm ends can be positioned such that the two winding axes of the two subwindings each lie in an arm tip.

In a particularly preferred embodiment, it is envisaged that the first and/or second separation element has an axial extent starting in the region of the outlet opening in the direction of the inlet opening. As a result, the double-axis winding of a Descemet's membrane is not only stabilized extremally at the outlet opening, but also over a length in front of it.

Here, it can be envisaged in a preferred embodiment that, in the direction from the outlet opening to the inlet opening, the cross section of the first and/or second separation element, viewed perpendicularly to the longitudinal extent of the tube, decreases, especially with the cross-sectional basic shape staying the same.

What is achieved as a result is that the forced guidance of the double-axis membrane winding is maximal only in the region of the outlet opening and gradually increases in the direction from the inlet opening to the outlet opening. In this connection, the first separation element is preferably formed around the central axis of the tube in the overwhelming region of said element's axial extent, preferably at each point of said element's axial extent. This brings about a stabilization of the winding in the central region of the device.

In a further preferred embodiment, it can be envisaged that the first separation element is floating in the cavity of the tube in a region close to the inlet opening, in particular has no connection to the inner wall of the tube when viewed in the cross section perpendicular to the longitudinal direction of extension, in particular thereby forms a spike onto which it is possible to mount a Descemet's membrane wound up to form a single winding.

This embodiment provides the particular advantage according to the invention that a Descemet's membrane can be introduced through the inlet opening into the device in the naturally preferably occupied single-axis winding form. In this connection, the one winding axis of the membrane preferably lies on the central axis of the tube or within the cross section of the first separation element floating in this region with no connection. As a result, the single-axis winding can be slid onto the thus formed spike of the separation element.

Preferably, the first separation element is connected to the preferably upper inner wall of the tube in a region close to the outlet opening, especially over an axial length of not more than 75%, preferably not more than 60%, further preferably not more than 50% and yet further preferably not more than 40% of the total axial length of the tube. In particular, the first separation element has, beyond this connection close to the outlet region, no further connection to the tube lying around it. In this connection, it can be envisaged that the length of the connection is in the range from 2 to 8 mm, in particular 4-6 mm.

What can be achieved by this type of connection is that a single-axis winding can be entirely positioned on the end region of the first separation element that is floating in the cavity or on the spike of said element.

What is then achieved by the increase in cross section of the first separation element in the direction of the outlet opening is that, when the single-axis winding is pushed forward in the direction of the outlet opening, the winding is spread open from the inside by the enlarging separation element. From the start of the connection of the separation element at the top at the inner wall of the tube, the two opposing membrane surface ends are then separated from one another and can each only wind up solitarily and thus form a double-axis winding of the membrane, which is then stabilized by the further shape of the separation element as described above.

The second separation element can, in the direction from the outlet opening to the inlet opening, exhibit a decreasing height above the outer wall of the tube; thus, it rises in height in the reverse direction and gradually shifts the membrane surface connecting the two windings in the direction of the central axis of the tube, this bringing about a further unwinding of the two subwindings.

Overall, it is thus possible with the device according to the invention for the Descemet's membrane to be introduced in a largely unwound state into the anterior chamber of the eye, and this considerably simplifies the further unwinding by the surgeon, even possibly making it unnecessary.

It can be further envisaged in the invention that at least the end of the tube with the inlet side has a connection interface for a syringe, for example a standard "Luer-Lock". This makes it possible for the membrane to be flushed out of the device and simultaneously unrolled by means of a liquid.

In a supplemental embodiment, it can be envisaged in the device that a channel, especially a channel which extends axially at least regionally, is arranged on or in the tube, in particular with the channel opening, at the outlet opening, into the edge end face of the tube. At every point, such a channel can be arranged preferably within the wall thickness of the tube and particularly preferably in the outlet-side end face of the tube. In a particularly preferred embodiment, such a channel is arranged in the lower region of the tube, especially in the cross-sectional region of a second separation element, if such an element is envisaged. However, the channel can also be arranged in the upper region of the tube, for example it can be arranged in the cross-sectional region of the first or else sole separation element. A position between the first and the second separation element is similarly possible.

There is thus the possibility of being able to put an air bubble, by means of the channel, under the membrane inserted into the eye anterior chamber, by the surgeon pushing air through the channel, for example by means of a syringe. Especially when the mouth opening of the channel lies below the membrane, a thus generated air bubble automatically lies under the membrane and pushes said membrane upward. Preferably, the channel can, in the direction of the inlet opening or at said opening, merge into a piece of tubing lying beyond the tube. At such a piece of tubing, it is, for example, possible to connect a syringe.

It can also be envisaged in the invention that a separation element, especially the upper sole separation element or at least the upper first separation element of two separation elements, is able to be pushed forward in an outward direction out of the region of the outlet opening. For this purpose, it can be envisaged in the invention that the slidable separation element lies in a guide extending in an axial direction in the tube, i.e., the direction between inlet and outlet opening. Here, the separation element can form a carriage which can glide on the guide, especially a rail-type guide.

This embodiment has the advantage that the separation element can be pushed forward out of the tube together with the membrane and that the separation element also still lies in or below the membrane within the eye. Especially with this embodiment, an above-described channel opening can be arranged in the separation element which is able to be pushed forward, in order to form via said channel an air bubble below the ejected membrane.

Similarly, it can be envisaged in the invention that, on one separation element, especially the upper separation element, at least one unrolling aid is envisaged at least to one side facing a subcavity, preferably to two opposite sides facing the subcavities, in particular the actuation of said unrolling aid simplifying the unrolling of the two windings of the membrane.

A particular unrolling aid can, for example, be the opening of a channel facing the subcavity, through which channel it is possible to eject liquid. The liquid jet thereby directed against the winding of the membrane can help to unroll the winding and to spread out the membrane.

An unrolling aid can also be in the form of a balloon which is expandable in the direction of the subcavity, for example as a result of pumping in a liquid or a gas and thereby pushes out the winding and unrolls it at the same time.

An unrolling aid can also be formed by actuatable lever elements, for example in the context of inverted scissors, and so the spreading of two levers unrolls the two opposite windings.

The embodiment with an unrolling aid is particularly advantageous in combination with a slidable separation element, but can also be used without said slidability.

For example, it can also be envisaged that an unrolling aid, upon actuation, not only moves in a purely lateral direction, i.e., to the subcavities, but also has an extension component in an axial direction to the front and is thus, upon actuation, also moved across the outlet opening and thus out of the tube. Thus, the unrolling aid promotes the unrolling of the windings outside the tube, even when the separation element is not movable.

It can also be envisaged in the invention that the device forms a set with a plunger element and that the plunger element is designed to slide an inserted membrane in the device in the direction of the outlet opening. For this purpose, the plunger element can be of such a deformability, especially elasticity, that it reproduces the change in shape of the cavity of the tube during forward pushing. For example, the plunger element can be formed from a foamed material.

The principle behind the invention and a specific preferred embodiment will be described on the basis of the figures.

DETAILED DESCRIPTION OF THE INVENTION

Figure 1:
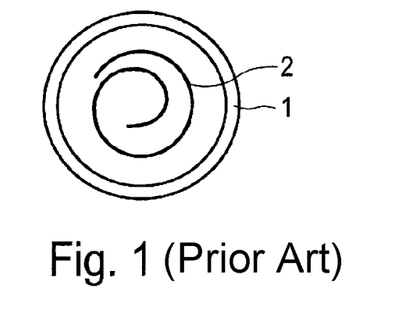
FIG. 1 shows a device according to the prior art.

FIG. 1 shows a device according to the prior art with a view of the outlet opening, comprising a tube 1 having a circular cross section. What can be visualized therein is a Descemet's membrane 2 which is wound up to form a single-axis winding and which is introducible as transplant into the anterior chamber of an eye. Evidently, the membrane retains its single-axis form and is inserted as such into the anterior chamber and unrolled therein with the disadvantages mentioned at the start.

Figure 2:
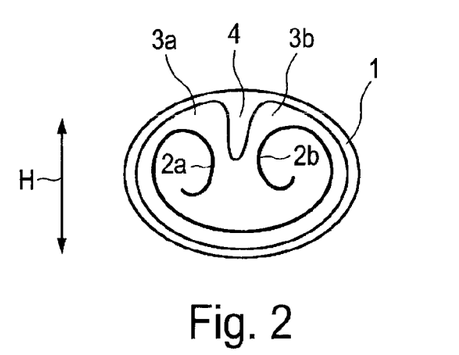
FIG. 2 shows an embodiment of the invention having a first separation element.

In the simplest embodiment, it can be envisaged in the invention to introduce the membrane, already as a double-axis winding, into the device and to stabilize it therein according to the embodiment of FIG. 2 and the following figures. Similarly, it is possible to introduce the membrane as a single-axis winding into the device and to transfer it therein to the double-axis wound form by forward pushing, especially as will be explained below on the basis of FIG. 6.

FIG. 2 shows a tube 1 having a flattened radial (i.e., in a plane orthogonal to the tube axis) cross section, i.e., in the vertical height direction H, the tube 1 is smaller than in the lateral (horizontal) direction. In all the figures, the tube can be seen to be oriented substantially horizontally, this corresponding to the customary position in an operation. All the cross sections shown are perpendicular to the longitudinal extent, apart from the section in the middle of FIG. 6.

From the upper region of the inner wall, a separation element 4 extends in a downward direction into the cavity of the tube 1 and divides the cavity, at least in the upper region, into two subcavities 3a and 3b. Said separation element 4 fits between the two subwindings 2a and 2b of an inserted membrane 2 and thus prevents the subwindings from being able to unroll over one another and from thereby automatically reshaping the membrane to form a single-axis winding.

Figure 3:
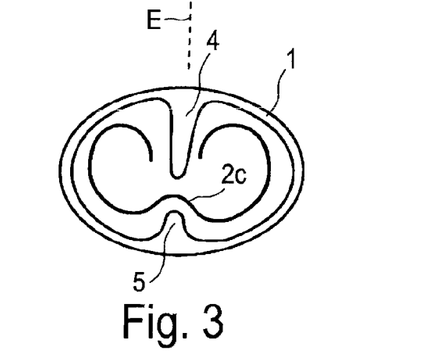
FIG. 3 shows an embodiment of the invention having first and second separation elements.

What can be visualized in FIG. 3 is a further development by lengthening the inner circumference of the inner wall of the tube 1 by a second separation element 5, which also laterally divides the cavity of the tube 1 in the lower region. Owing to the part of the second separation element 5 that is rising as a projection, a membrane surface region 2c connecting the two windings is shifted upward and each of the two windings is thus further unwound.

The two separation elements directly face each other and are preferably symmetrical around the vertical plane E running in the axial direction.

Figure 4:
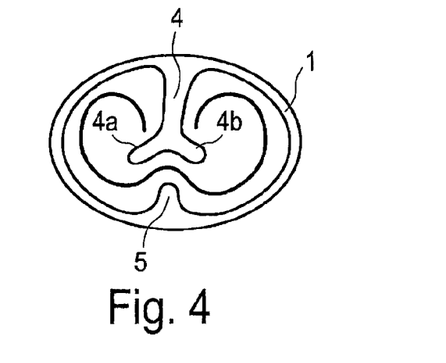
FIG. 4 shows an embodiment of the invention having a first separation element of another configuration and a second separation element.

What can be visualized in FIG. 4 is a further embodiment in which the first separation element 4 viewed in cross section branches perpendicularly to the axial direction of the tube to form two opposing sides and forms arms 4a and 4b, which point downward here in an arm starting region. Here, the branching preferably starts in the region of the central axis of the tube 1.

Figure 5:
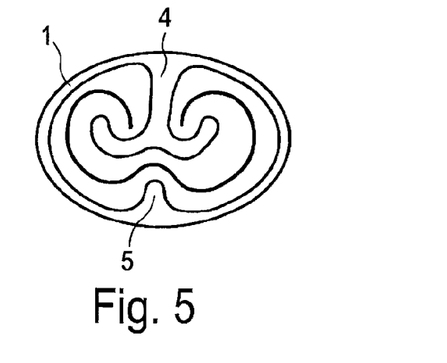
FIG. 5 shows an embodiment of the invention having a first separation element of yet another configuration and a second separation element.

FIG. 5 shows a further development in which each of the arms 4a, 4b is curved in an upward direction at its end. As a result, each of the arm ends engages in the respective subwinding of the membrane 2. This generates a maximum guidance of the membrane surface in the spatial region remaining free between the separation elements 4 and 5 and forces the membrane to the at least partial unwound state, and so its further unwinding after introduction into the anterior chamber of an eye is substantially simplified.

What can be visualized in FIGS. 1 to 5 is the configuration of the devices in a cross-sectional plane in the region of the outlet opening. However, the shaping shown is exhibited by the separation elements not only here, but also in an axial direction of extension proceeding from the outlet opening in the direction of the inlet opening, with the cross-sectional area of the two separation elements decreasing in this direction.

Figure 6:
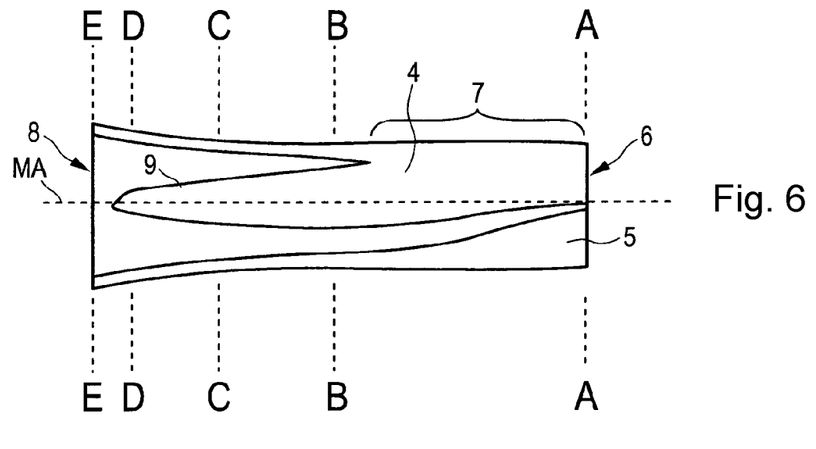
FIG. 6 shows a preferred embodiment of the invention in axial cross-section.

FIG. 6 shows this configuration on a preferred embodiment of the invention firstly in a central vertical cut made along the central axis MA of the tube 1 and at multiple sectional positions perpendicular thereto.

It can be seen in the middle section of FIG. 6 that the second separation element 5 rises in height above the outer wall of the tube 1 in the direction of the outlet opening 6 (rightwards here). The first separation element 4 is formed around the central axis MA of the tube 1 over the overwhelming part of said element's axial extent, if not entirely, and, in this connection, is only connected to the upper inner tube wall in a part 7 close to the outlet opening 6 and floating freely in the cavity in the region close to the inlet opening 8, forming there a spike 9 which tapers in the cross section and on which the Descemet's membrane can be slid as a single-axis winding. The first and/or the second separation element 4, 5 can be of the same material as the tube wall, in particular form one piece therewith.

Figure 6A:
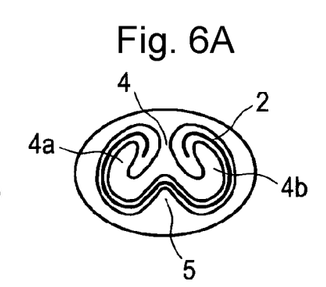
FIGS. 6A, 6B, 6C, 6D and 6E are respective cross-sections of the embodiment of FIG. 6 taken on respective planes A-A, B-B, C-C, D-D, and E-E perpendicular to the plane of FIG. 6.
Figure 6B:
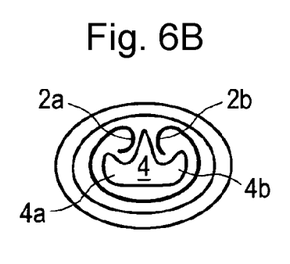
Figure 6C:
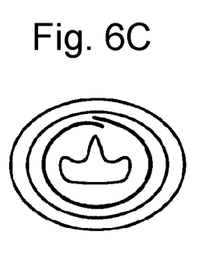
Figure 6D:
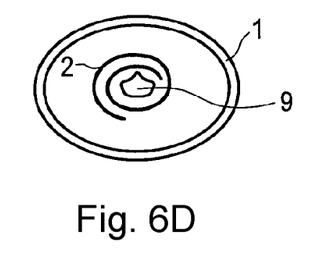
Figure 6E:
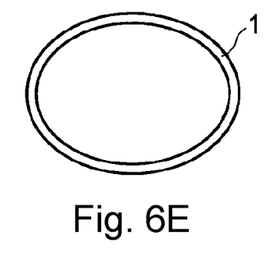

FIG. 6E shows, in section E-E of FIG. 6, the inlet opening with a completely free cross section and FIG. 6D shows, in section D-D of FIG. 6, this single-axis winding of the membrane 2 in the arrangement around the spike 9 of the first separation element 4.

If, then, the membrane 2 in the device is moved in the direction of the outlet opening 6, the cross-sectional broadening of the first separation element 4 causes the winding to spread open from the inside and the membrane surface overlap to decrease as result, as shown by FIG. 6C, which is section C-C of FIG. 6.

With further forward pushing, the shaping of the first separation element 4 causes the membrane overlap to be removed and two subwindings 2a, 2b to form in the region of the upper subcavities between the arms 4a, 4b and the tube wall, as illustrated by FIG. 6B, which is section B-B of FIG. 6. Here, the subwindings 2a, 2b can themselves still be overlapping.

The rising second separation element 5, which also laterally divides the tube cavity in the lower region, causes a further unwinding of the membrane 2 by shifting the membrane 2 upward in the region between the subwindings, as shown by FIG. 6A, which is the section A-A at the outlet opening of FIG. 6. This sectional representation substantially corresponds to the representation in FIG. 5.

It can be clearly seen that the device in this embodiment offers the advantage of inserting a membrane 2 as a single-axis winding into the device and of being able to introduce it as a partially unrolled double-axis winding into the anterior chamber of the eye, the conversion from the single-axis winding to the double-axis winding being effected automatically in the device by the guidance of the membrane surfaces between the separation elements 4, 5 and the spatial regions formed therebetween.

In this connection, the configuration can be effected such that the inner circumferential length of the tube, which is formed in the regions between both separation elements 4, 5 and the first separation element 4 and the inner wall of the tube 1, is greater than the diameter of the membrane 2, in particular is greater than 8 or even 9 mm, and so there are no more directly overlapping membrane surface regions in a membrane 2 guided in the device.

In particular, this can be achieved when the cross section perpendicular to the tube-based longitudinal axis of the free spatial region in the tube that is formed for membrane guidance corresponds, at least in the region of the outlet opening, to the shape of a W, of a wave or of the small Greek letter omega (ω).

Figure 7:
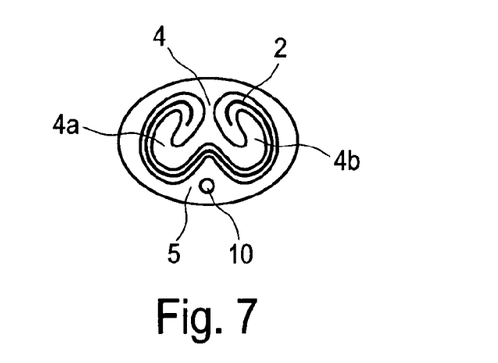
FIG. 7 shows another embodiment of the invention in cross-section taken on the plane of the outlet opening of the tube.

FIG. 7 shows a possible further development, according to which a channel is arranged in the tube in the lower region, preferably in the wall thickness around the vertical central plane, the mouth opening 10 of said channel being in the annular end face at the outlet opening, in this case preferably even within the cross-sectional area of the second separation element.

The channel can lie longitudinally in the direction of the tubular extent and be used to spray air under the membrane. For this purpose, the channel can be connectable to a syringe, for example via an external tubing connector into which the channel merges.

Figure 8:
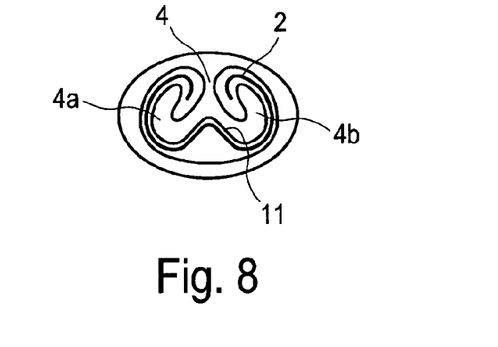
FIG. 8 shows yet another embodiment of the invention in cross-section taken on the plane of the outlet opening of the tube.

FIG. 8 discloses a further alternative in which all the features of the embodiments so far can be realized with the exception of the second separation element, which is not envisaged here. Guidance of the membrane over the first and sole separation element 4 is enough to be able to cause the membrane in the lower surface region connecting the two subwindings to automatically fold upward owing to inner tensions, without a second separation element being required for this purpose. Nevertheless, the first separation element has in its lower region, especially where it branches in this embodiment, an upwardly pointing recess 11 into which this membrane surface region can enter.

As in the case of FIG. 7, it would also be possible here for a channel opening 10 to lie in the lower tube wall within the wall thickness; however, it is not visualized here.

Figure 9:
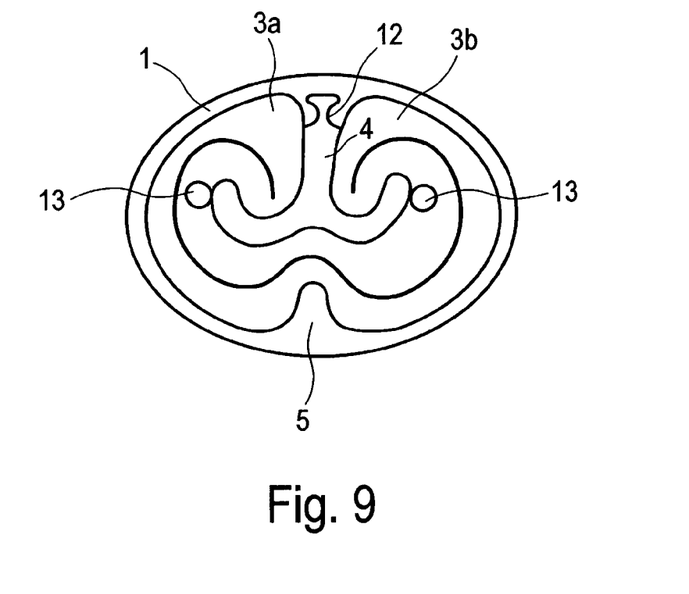
FIG. 9 shows yet another embodiment of the invention.

FIG. 9 shows one embodiment in which the separation element 4 is slidably arranged in a guide 12 formed between the tube and the separation element 4. As a result, the separation element 4 can be slid in the axial direction of the tube out of its outlet opening.

In addition, it is possible to see here the further development where an unrolling aid 13 is arranged on both sides of the separation element 4 and facing the respective subcavities 3a and 3b. Here, the unrolling aid 13 is designed as an expandable balloon 13 which can be supplied with a fluid from the outside via a channel in the separation element that is not shown.

When the balloon 13 expands, it pushes out the respective winding of the membrane and causes its unrolling.

The invention claimed is:

1. A device for transplantation of a Descemet's membrane, comprising a longitudinal tube having an inner cavity, an inlet opening configured for introduction of the Descemet's membrane into the tube, and an outlet opening configured for ejection of the Descemet's membrane from the device, wherein the tube has, at least in a region of the outlet opening, a separation element which protrudes from an inner wall region of the tube into the cavity, the separation element dividing the inner cavity at least regionally, the separation element is floating in the inner cavity in a region close to the inlet opening, the separation element having no connection to the inner wall of the tube when viewed in a cross-section perpendicular to a longitudinal extent of the tube, and in a direction from the outlet opening to the inlet opening the cross-section of the separation element, viewed perpendicularly to the longitudinal extent of the tube, is decreasing thereby forming a spike configured to receive the Descemet's membrane thereon in a form of a single winding.

2. The device as claimed in claim 1, wherein the inner cavity is, in an axially extending region contiguous with a region of the outlet, divided in an upper region into two laterally adjacent subcavities which are separated by the separation element and which are connected to one another in an underlying region.

3. The device as claimed in claim 2, wherein the separation element is connected to the inner wall of the tube only in the region of the inner wall of the tube proximate the region of the outlet opening over an axial length of not more than 75% of a total axial length of the tube, the connection being configured to form a double-axis winding of the membrane from a single-axis winding by separating two opposing surface ends of the membrane from a start of the connection at a top of the inner wall of the tube.

4. The device as claimed in claim 3, wherein at least one unrolling aid facing one of the subcavities is provided on the separation element, the unrolling aid being configured to be actuated to effect unrolling of the double-axis winding of the membrane, the unrolling aid being formed by
   a. an opening of the channel facing the subcavity, the channel being configured for ejection of a liquid therefrom, or
   b. a balloon configured to expand in a direction of the subcavity, or
   c. actuatable lever elements.

5. The device as claimed in claim 2, wherein the tube has, at least in the region of the outlet opening, a flattened outer cross-section with a smaller cross-sectional extent in a vertical height direction than in a horizontal direction.

6. The device as claimed in claim 5, wherein, at least in the region of the outlet opening, the separation element has on a bottom end thereof a recess which points upward.

7. The device as claimed in claim 6, wherein, the tube, at least in the region of the outlet opening, has a second separation element which protrudes into the inner cavity from the inner wall region of the tube and which divides the inner cavity at least regionally, with the second separation element being opposite the separation element.

8. The device as claimed in claim 7, wherein, in a direction from the outlet opening to the inlet opening, a cross-section of the second separation element, viewed perpendicularly to the longitudinal extent of the tube, decreases.

9. The device as claimed in claim 7, wherein the second separation element, in the direction from the outlet opening to the inlet opening, has a decreasing height with respect to an outer wall of the tube.

10. The device as claimed in claim 1, wherein, at least in the region of the outlet opening, the separation element is branched on its bottom and forms a respective arm on each side of a vertical central plane.

11. The device as claimed in claim 10, wherein, at least in the region of the outlet opening, each of the arms forms a curve which points upward.

12. The device as claimed in claim 1, wherein the separation element has an axial extent starting in the region of the outlet opening in a direction of the inlet opening.

13. The device as claimed in claim 12, wherein the separation element is formed around a central axis of the tube at each point of the axial extent of the separation element.

14. The device as claimed in claim 1, wherein a channel which extends axially at least regionally, is arranged on or in the tube, an outlet opening of the channel being in an edge end face of the tube, the channel, in a direction of the inlet opening, merging into a piece of tubing situated beyond the tube.

15. The device as claimed in claim 1, wherein the separation element is configured to be slid forward in an outward direction out of the region of the outlet opening, the separation element being situated in a guide extending in an axial direction in the tube.

* * * * *